United States Patent [19]

Bapat

[11] Patent Number: 5,534,552
[45] Date of Patent: Jul. 9, 1996

[54] CLEAR NON-ALCOHOLIC SINUS AND ALLERGY MEDICATION

[75] Inventor: Swati Bapat, Willowdale, Canada

[73] Assignee: Warner-Lambert Company, Morris Plains, N.J.

[21] Appl. No.: 205,055

[22] Filed: Mar. 2, 1994

[51] Int. Cl.[6] ............ A61K 9/08; A61K 31/13; A61K 47/00; A61K 47/10
[52] U.S. Cl. ............ 514/667; 514/849; 514/850; 514/852; 514/853; 514/855
[58] Field of Search .................................... 514/667

[56] References Cited

U.S. PATENT DOCUMENTS

| | | | |
|---|---|---|---|
| 2,427,878 | 9/1947 | Rieveschl, Jr. . | |
| 3,134,720 | 5/1964 | Green et al. | 167/82 |
| 3,608,063 | 9/1971 | Banker | 424/22 |
| 3,927,205 | 12/1975 | Ohno et al. | 424/80 |
| 4,427,681 | 1/1984 | Munshi | 424/260 |
| 4,642,231 | 2/1987 | Peters et al. | 424/15 |
| 4,749,700 | 6/1988 | Wenig | 514/223.2 |
| 4,753,800 | 6/1988 | Mozda | 424/440 |
| 4,892,877 | 1/1990 | Sorrentino . | |
| 5,112,604 | 5/1992 | Beaurline et al. | 424/490 |
| 5,196,436 | 3/1993 | Smith | 514/289 |
| 5,272,137 | 12/1993 | Blase et al. | 514/54 |
| 5,314,915 | 5/1994 | Rencher | 514/535 |

FOREIGN PATENT DOCUMENTS 620001  10/1994  European Pat. Off. ......... A61K 9/00

OTHER PUBLICATIONS

Kumar et al PEDIATRICS 91(5):927–933 May 1993.
Aldridge et al [I] BR. J. DERMATOL 110(3):351–355 (1984).
Aldridge et al [II] BR. J. DERMATOL 102(5):545–549 (1980).
Ribon et al ann. allergy 44(4):220–224 (1980).
Fisher J. AM. ACAD. DERMATOL 3(3):303–306 (1980).

*Primary Examiner*—Shep K. Rose
*Attorney, Agent, or Firm*—Jean B. Barish

[57] ABSTRACT

A clear, hypoallergenic sinus and allergy medication is orally administered in an aqueous, liquid dosage form. The formulation provides effective sinus and allergy relief without alcohol or dyes which adversely affect many allergy sufferers. Said relief is provided while still maintaining aesthetic appeal or pleasant taste and texture.

17 Claims, No Drawings

CLEAR NON-ALCOHOLIC SINUS AND ALLERGY MEDICATION

FIELD OF THE INVENTION

The present invention relates to allergy and sinus medications which are orally administered in liquid dosage forms that are easy to swallow, taste good and provide immediate and long lasting relief. Such medications generally contain as the active ingredient an antihistamine which is otherwise bitter tasting and unpalatable yet is effective in clearing up blocked sinuses, and itchy, watery eyes. The medications then must contain numerous taste modifiers, color enhancers and dyes which are necessary to make the medication more appealing, particularly with respect to children.

BACKGROUND OF THE INVENTION

One of the major problems that exists in the art of pharmacy is that many patients, particularly young children and older adults, are unwilling and/or unable to swallow tablets, capsules or other solid dosage forms of medication. Liquid cold/sinus preparations are admittedly not novel and numerous commercially available formulations exist in the marketplace. Benadryl®, Vicks®, Sudafed®, Dimetapp® and others are all well known liquid cold remedies that are easily swallowed and do not possess the problems inherent in swallowing a tablet which causes difficulty for young children and older patients. These cold/sinus remedies vary with respect to what actives are present, but many include a decongestant, an antihistamine, an expectorant, an analgesic and the like either singly or in combination depending upon the relief sought.

The problem that exists with respect to many of these actives is that they are not very soluble in water and therefore require some type of organic solvent such as alcohol for dissolution and dispersion throughout the liquid formulation. Another problem that is inherent with these cold medications is the bad taste of the actives and therefore measures must be taken to flavor the liquid in some way so as to taste-mask the active and prevent its perception by the patient. If these drawbacks are not resolved, high degrees of patient compliance cannot be assured.

Co-pending applications Ser. Nos. 08/072,614 and 08/123,402 disclose and claim non-alcohol cold and sinus medications in which the active antihistamine and decongestant are solubilized through the use of an emulsifier/surfactant which, together with other ingredients in specified ratios yield a product that provides effective relief of cold/sinus symptoms yet still tastes good and imparts a smooth, lubricous mouthfeel.

U.S. Pat. No. 4,892,877 to Sorrentino discloses a cough-sore throat medication comprising an aqueous-based liquid preparation comprising an antitussive such as dextromethorphan and a known topical anesthetic such as phenol. Although water serves as the main carrier in the formulation, an alcoholic co-solvent is also required up to 25%.

U.S. Pat. No. 5,112,604 to Beaurline et. al. discloses a sustained release oral formulation for an active drug, in particular, theophylline, an antiasthmatic. The drug is maintained in an aqueous suspension through the use of a hydrocolloid gum/silicon dioxide suspending agent. A polymeric particle system such as polyvinyl pyrrolidone, polyvinylalcohol, acrylic acid and the like are necessary as a dispersing agent in a 70% sorbitol carrier solution.

The need for using high levels of alcohol as a solvent and as a flavor enhancer in the formulation which serves no therapeutic purpose has recently been questioned in that consumption of alcohol in any form has never been regarded as highly beneficial to ones health. Nevertheless, the conventional carrier for the active and flavor ingredients in most cold/sinus medications is typically a water:alcohol mixture. Generally, the ratio of water to alcohol is in the range of from about 1:1 to about 20:1 and most commonly from about 3:1 to about 10:1. The typical amount of the water:alcohol mixture comprising the cold/sinus formulation ranges from about 50% to about 99.9% of the entire composition by weight. In light of these amounts of alcohol present in most formulations, it is obviously beneficial to make non-alcohol based liquid medications available.

However, it has also come to light that many of those who use antihistamine medications were taking them for allergy relief and were thereby also sensitive to many other potential allergens. It was realized that the inclusion of various dyes for color in these formulations sometimes compounded the allergic reaction and therefore the medication did not necessarily alleviate it. Removal of these compounds would be a further advantage as the absence of dye could not lead to additional allergic reaction. One would expect however, that the previously grape or cherry-colored syrups would lose their aesthetic appeal. Surprisingly, the present invention provides a clear, colorless liquid that imparts a natural, wholesome constituency which can only enhance greater patient compliance.

SUMMARY OF THE INVENTION

The present invention is a clear alcohol free hypoallergenic sinus medication that is effective in the relief of those symptoms associated with allergies that lacks the dyes and other excipients previously found in similar sinus and allergy compositions which can further aggravate those symptoms. Its surprising crystal clarity remains aesthetically appealing even without the colors heretobefore thought necessary.

DETAILED DESCRIPTION OF THE INVENTION

The present invention is an effective allergy relief medication that is clear and lacking many of the additives and colorants present in compositions of the prior art which were unexpectedly found to exacerbate many of the sinus and allergy symptoms the medication was actually meant to relieve.

This is accomplished while maintaining a nonalcoholic aqueous carrier solvent for administration of the active yet still solubilizing and stabilizing the antihistamine during manufacture, storage and delivery. The preferred antihistamine of choice is diphenhydramine hydrochloride (2-diphenyl methoxy-$N_1N$-dimethylethanamine hydrochloride) which consists of the following chemical structure:

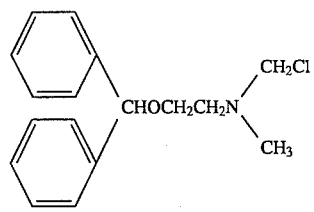

The antihistamines chemical characteristics and method of preparation are disclosed in U.S. Pat. No. 2,427,878 to Rieveschal, Jr., which is hereby incorporated by reference.

The amount of antihistamine incorporated in the composition may vary but generally will comprise from about 0.05% w/v to about 0.2% w/v of the total weight of the composition and preferably from about 0.10% to about 0.15% w/v and most preferably, about 0.125% w/v of the total composition.

The antihistamine can be solubilized in water alone which comprises the greatest component of the medication, approximately 50% w/v of the total weight thereof. Actually, the precise amount will be determined according to the total amount of the other components used, as the water will be added in an amount to bring the total w/v to 100%. Generally, this will comprise from about 45% w/v to about 55% w/v of the total weight of the formulation.

Many of the standard, sugar based sweeteners and bulking agents of formulations known in the art have also been removed in order to provide a non-caloric and non-cariogenic composition. As a result of the removal of these ingredients, much of the bulk and body of the liquid medication is missing and must be replaced in order to provide a desirable mouthfeel and texture. To this end, thickeners such as sodium carboxymethyl cellulose are added in amounts of from approximately 0.1% w/v to about 0.3% w/v of the total composition, and preferably from about 0.15% w/v to about 0.25% w/v and most preferably in an amount of about 0.20% w/v of the total formulation.

The liquid formulations of the present invention also include a humectant composition to give the liquid greater viscosity and stability. Suitable humectants useful in the formulations of the present invention include glycerin, polyethylene glycol, propylene glycol and mixtures thereof. Preferably, glycerin is used and incorporated in an amount of from about 2.0% w/v to about 15% w/v and preferably in an amount of from about 4.0% w/v to about 8.0% w/v of the entire composition and most preferably in an amount of about 6.0% w/v of the total composition.

Generally, liquid sinus and allergy medications are bottled or packaged and stored for considerable periods of time. These storage periods may occur in warehouse or store shelf environments, as well as even after the point of sale when the medication may sit around for months or even years in the bathroom or kitchen cabinet. In these situations, the long shelf life requirements may result in further stability problems, and additional preservatives, stabilizers, flavor modifiers, acidifiers, pH adjusters and the like may be incorporated as necessary. The specific agents, such as sodium benzoate as a preservative and citric acid and sodium citrate as pH buffers are well known in the art and may be added in amounts as dictated by standard pharmacological practice.

In order to make the liquid allergy and sinus formulations more palatable, flavors and sweeteners may also be added according to taste. Surprisingly, there is no need for flavor enhancers or taste-masking agents as required for the antihistamine compositions of the prior art. Suitable sweeteners include water-soluble artificial sweeteners such as saccharin salts, cyclamate salts, acesulfame-K, monoammonium glycyrrhizinate and mixtures thereof. Other suitable sweetening agents include aspartame, sucralose, protein based sweeteners such as thymidine, monellin and the like.

In general, the effective amount of sweetener employed will vary according to what type of sweetener is used and is utilized to provide the level of sweetness desired for a particular flavor of liquid formulation. The amount will normally comprise from about 0.01% w/v to about 5.0% w/v and preferably from about 0.01% w/v to about 1.0% w/v of the entire composition. Sodium saccharin is the preferred sweetener of choice and will preferably be incorporated in an amount of from about 0.01% w/v to about 0.5% w/v of the weight of the entire composition and most preferably in an amount of about 0.06% w/v of the total composition.

The flavoring (flavoring agents) that may be used include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, oil of wintergreen (methyl salicylate), peppermint oil, clove oil, bay oil, eucalyptus oil, thyme oil, cedar leaf oil, oil of nutmeg, oil of sage, and oil of bitter almond. Also useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, apricot and so forth. These flavorings may be used individually or in admixture. Commonly used flavors include mints such as peppermint, menthol, artificial vanilla, cinnamon derivatives, and various fruit flavors whether employed individually or in admixture.

Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive such as those described in "Chemicals Used in Food Processing" pub. 1274 by the National Academy of Sciences, pages 63–258 may be used.

Further examples of aldehyde flavorings include but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e. piperonal (vanilla, cream); vanillin (vanilla, cream); alpha-amyl cinnamaldehyde (spicy fruity flavors); butyraldehyde (butter, cheese); valeraldehyde (butter, cheese); citronella (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2,6-dimethyloctanal (green fruit); and 2-dodecenal (citrus, mandarin); cherry; grape; mixtures thereof and the like.

The amount of flavoring employed is normally a matter of preference subject to such factors as flavor type, individual flavor, and strength desired. Thus, the amount may be varied in order to obtain the result desired in the final elixir product. Such variations are within the capabilities of those skilled in the art without the need for undue experimentation. In general, amounts of about 0.05% to about 2.0% by weight of the composition are useable with amount of about 0.05% to 1.5% being preferred.

The following examples are provided to more specifically teach and better define the formulations of the present invention. They are for illustrative purposes only and it is realized that minor changes and variations can be made that are not disclosed therein. Such alternatives are still to be considered as falling within the spirit and scope of he present invention as recited by the claims that follow.

Example I

The following components were collected in their respective amounts

| Per | Ingredients | Percent W/V | Ingredient 3 L | Quantity 5 ml. |
|---|---|---|---|---|
| 1. | Sodium Carboxy Methyl Cellulose USP Type 7MF | 0.20 | 6.0 g. | 10.0 mg. |
| 2. | Glycerin 99% (CP Grade) | 12.5 | 375.0 g. | 635 mg. |
| 3. | Sodium Citrate USP Gran. Hdy | 0.75 | 22.5 g. | 37.5 mg. |
| 4. | Sodium Saccharin USP Powder | 0.06 | 1.0 g. | 3.0 mg. |
| 5. | Sodium Benzoate NF | 0.5 | 15.0 g. | 25.0 mg. |
| 6. | Citric Acid Anhyd. USP Gran. | 0.40 | 12.0 g. | 20.0 mg. |
| 7. | Sorbitol Solution USP | 45.0 | 1.35 Kg. | 2250 mg. |
| 8. | Diphenhydramine Hydrochloride | 0.125 | 3.75 g. | 6.25 mg. |
| 9. | Art. Fruit Punch Flavor FAAF896 (F&C Int'l) | 0.32 | 9.6 g. | 16.0 mg. |
| 10. | Deionized Water | qs 100 ml. | qs 3 L | qs 5 ml. |

The sodium carboxymethylcellulose was first mixed in 900 mls. of the deionized water in a five (5) liter stainless steel mixing bowl. Once well dispersed, the glycerin, sodium citrate, saccharin, sodium benzoate, sorbitol and diphenhydramine were added and blended thoroughly. The citric acid anhydride was then slowly mixed in and again, blended well before adding the final flavor ingredient. Additional water was then added to raise the final volume to three (3) liters.

Each 5 ml. aliquot of the medication delivers 6.25 mgs. of the active diphenhydramine hydrochloride for systemic relief of blocked sinuses, runny nose and itchy, watery eyes commonly associated with allergies and hay fever. The composition was odorless and clear in color and presented a sweet, fruity taste at a slightly acidic pH of 4.5–4.9.

What we claim is:

1. A clear aqueous non-alcoholic sinus and allergy medication free of dyes comprising diphenhydramine hydrochloride in an amount from about 0.05% w/v to about 0.20% w/v of the total composition, the humectants glycerin and sorbitol, the glycerin being in the amount from about 10.0% w/v to about 15% w/v of the total composition, carboxymethylcellulose in an amount from about 0.1% w/v to about 0.3% w/v of the total composition, an effective amount of citric acid and sodium citrate, and flavor agents.

2. The sinus and allergy medication of claim 1 wherein said diphenhydramine hydrochloride comprises from about 0.10% w/v to about 0.20% w/v of the total composition.

3. The sinus and allergy medication of claim 2 wherein said diphenhydramine hydrochloride comprises approximately 0.20% w/v of the total composition.

4. The sinus and allergy medication of claim 1 wherein said glycerin comprises approximately 15% w/v of the total composition.

5. The sinus and allergy medication of claim 1 wherein said thickener is in an amount from about 0.15% w/v to about 0.25% w/v of the total composition.

6. A clear aqueous, hypoallergenic sinus and allergy medication free of dyes that is alcohol free comprising diphenhydramine hydrochloride in an amount from about 0.05% w/v to about 0.15% w/v of the total composition, the humectants glycerin and sorbitol the glycerin being in the amount from about 10.0% w/v to about 15% w/v of the total composition, carboxymethylcellulose in an amount from about 0.1% w/v to about 0.3% w/v of the total composition, sodium citrate in an amount of about 0.75% w/v of the total composition, citric acid in an amount of about 0.40% w/v of the total composition, flavors and preservatives.

7. The sinus and allergy medication of claim 6 wherein said diphenhydramine hydrochloride comprises from about 0.10% w/v to about 0.20% w/v of the total composition.

8. The sinus and allergy medication of claim 6 wherein said diphenhydramine hydrochloride comprises approximately 0.20% w/v of the total composition.

9. The sinus and allergy medication of claim 6 wherein said glycerin comprises from about 15% w/v of the total composition.

10. The sinus and allergy medication of claim 6 wherein said thickener is in an amount from about 0.15% w/v to about 0.25% w/v of the total composition.

11. A cleary aqueous, hypoallergenic sinus and allergy medication free of dyes that is alcohol free comprising diphenhydramine hydrochloride in an amount from about 0.10% w/v to about 0.20% w/v of the total composition, a humectant wherein the humectant is glycerin, the humectant being in the amount from about 10.0% w/v to about 15% w/v of the total composition, carboxymethylcellulose in an amount from about 0.1% w/v to about 0.3% w/v of the total composition, sodium citrate in an amount of about 0.75% w/v of the total composition, citric acid anhydrous in an amount of about 0.40% w/v of the total composition and sorbitol in an amount of about 45% w/v of the total composition.

12. The sinus and allergy medication of claim 11 wherein the diphenhydramine hydrochloride is in an amount of about 0.20% w/v of the total composition.

13. The sinus and allergy medication of claim 12 wherein the humectant is in an amount from about 15% w/v.

14. The sinus and allergy medication of claim 13 wherein the carboxymethylcellulose is in an amount of about 0.20% w/v of the total composition.

15. The sinus and allergy medication of claim 14 further comprising sodium saccharin in the amount of about 0.06% w/v of the total composition.

16. The sinus and allergy medication of claim 15 further comprising sodium benzoate in the amount of about 0.5% w/v of the total composition.

17. The sinus and allergy medication of claim 16 further comprising at least one flavor.

* * * * *